(12) United States Patent
Tracey et al.

(10) Patent No.: US 7,741,372 B2
(45) Date of Patent: Jun. 22, 2010

(54) GUANYLHYDRAZONES USEFUL FOR TREATING DISEASES ASSOCIATED WITH T CELL ACTIVATION

(75) Inventors: Kevin J. Tracey, Old Greenwich, CT (US); Pamela Cohen, Tenafly, NJ (US); Michael Bukrinsky, Glen Head, NY (US); Helena Schmidtmayerova, New York, NY (US)

(73) Assignee: Cytokine PharmaSciences, Inc., King of Prussia, PA (US)

( * ) Notice: Subject to any disclaimer, the term of this patent is extended or adjusted under 35 U.S.C. 154(b) by 1390 days.

(21) Appl. No.: 10/619,426

(22) Filed: Jul. 16, 2003

(65) Prior Publication Data

US 2004/0171695 A1    Sep. 2, 2004

Related U.S. Application Data

(60) Continuation of application No. 09/705,581, filed on Nov. 2, 2000, now Pat. No. 6,673,777, which is a division of application No. 08/970,973, filed on Nov. 14, 1997, now Pat. No. 6,143,728.

(60) Provisional application No. 60/031,061, filed on Nov. 15, 1996.

(51) Int. Cl.
   *A61K 31/15*     (2006.01)
   *A61K 31/155*    (2006.01)
   *A61K 31/505*    (2006.01)
   *A61K 45/06*     (2006.01)

(52) U.S. Cl. .................. 514/632; 514/934; 514/274

(58) Field of Classification Search ............. 514/632, 514/274, 934
See application file for complete search history.

(56) References Cited

U.S. PATENT DOCUMENTS

| 5,574,040 | A | * | 11/1996 | Bukrinsky et al. ........... 514/275 |
| 5,599,984 | A |   | 2/1997  | Bianchi et al. |
| 5,616,578 | A | * | 4/1997  | Otto ........................... 514/218 |
| 5,750,573 | A |   | 5/1998  | Bianchi et al. |
| 5,753,446 | A |   | 5/1998  | Johnson |
| 5,753,684 | A |   | 5/1998  | Bianchi et al. |
| 5,849,794 | A |   | 12/1998 | Bianchi et al. |
| 5,854,289 | A | * | 12/1998 | Bianchi et al. ............... 514/615 |
| 5,859,062 | A |   | 1/1999  | Bianchi et al. |
| 6,008,255 | A |   | 12/1999 | Bianchi et al. |

(Continued)

OTHER PUBLICATIONS

Bianchi et al. An inhibitor of macrophage arginine transport and nitric oxide production (CNI-1493) prevents acute inflammation and endotoxin lethality. Molecular Medicine (Baltimore, MD, United States) (1995), 1(3), 254-66.*

(Continued)

*Primary Examiner*—Yvonne L Eyler
*Assistant Examiner*—Donna Jagoe
(74) *Attorney, Agent, or Firm*—John K. Pike; Law Office of John K. Pike, PLLC (57) ABSTRACT

There is disclosed a method for treating diseases and disorders involving T cell activation and HIV-infection using the p38 mitogen activated protein kinase (MAPK) signaling pathway as a target for intervention. There is further disclosed a use for guanylhydrazone-substituted compounds to treat diseases and disorders related to T cell activation and HIV-infection.

20 Claims, 5 Drawing Sheets

U.S. PATENT DOCUMENTS

| | | | |
|---|---|---|---|
| 6,022,900 A | 2/2000 | Bianchi et al. | |
| 6,143,728 A | 11/2000 | Tracey et al. | |
| 6,180,676 B1 | 1/2001 | Bianchi et al. | |
| 6,218,136 B1* | 4/2001 | Kumar et al. | 435/15 |
| 6,248,787 B1 | 6/2001 | Bianchi et al. | |
| 6,673,777 B1* | 1/2004 | Tracey et al. | 514/44 |

OTHER PUBLICATIONS

Levine et al. Mitoguazone therapy in patients with refractory or relapsed AIDS-related lymphoma: results from a multicenter phase II trial. J Clin Oncol. Mar. 1997;15(3):1094-103.*

Kumar et al. Activation of the HIV-1 Long Terminal Repeat by Cytokines and Environmental Stress Requires an Active CSBP/p38 MAP Kinase. The Journal of Biological Chemistry (271), No. 48. pp. 30864-30869. Nov. 29, 1996.*

Bianchi et al., Suppression of Proinflammatory Cytokines in Monocytes by a Tetravalent Guanylhydrazone, J. Exp. Med. vol. 183 Mar. 1996 pp. 927-936.*

Barré-Sinoussi, F., et al., "Isolation of a T-Lymphotropic Retrovirus from a Patient at Risk for Acquired Immune Deficiency Syndrome (AIDS)", Science, vol. 220, pp. 868-870 (1983).

Gallo, R.C., et al., "Frequent Detection and Isolation of Cytopathic Retroviruses (HTLV-III) from Patients with AIDS and at Risk for AIDS", vol. 224, pp. 500-503 (1984).

Teich, N., et al., "RNA Tumor Viruses", Weiss, et al., eds., Cold Spring Harbor Laboratory, pp. 949-956 (1984).

Mitsuya, H., et al., "Molecular Targets for AIDS Therapy", Science, vol. 249, pp. 1533-1544 (1990). (cited as "1991" in specification).

Larder, B.A., et al., "HIV with Reduced Sensitivity to Zidovudine (AZT) Isolated During Prolonged Therapy", Science, vol. 243, pp. 1731-1734 (1989). (cited in specification as "Lander et al.").

Erickson, J., et al., "Design, Activity, and 2.8 Å Crystal Structure of a $C_2$ Symmetric Inhibitor Complexed to HIV-1 Protease", Science, vol. 249, pp. 527-533 (1990).

Marshall, C.J., et al., "Specificity of Receptor Tyrosine Kinase Signaling: Transient Versus Sustained Extracellular Signal-Regulated Kinase Activation", Cell, vol. 80, pp. 179-185 (1995).

Galcheva-Gargova, Z., et al., "An Osmosensing Signal Transduction Pathway in Mammalian Cells", Science, vol. 265, pp. 806-808 (1994).

Kyriakis, J.M., et al., "The Stress-Activated Protein Kinase Subfamily of c-Jun Kinases", Nature, vol. 369, pp. 156-160 (1994).

Raingeaud, J., et al., "Pro-Inflammatory Cytokines and Environmental Stress Cause p38 Mitogen-Activated Protein Kinase Activation by Dual Phosphorylation on Tyrosine and Threonine", The Journal of Biological Chemistry, vol. 270, No. 13, pp. 7420-7426 (1995).

Han, J., et al., "A MAP Kinase Targeted by Endotoxin and Hypersmolarity in Mammalian Cells", Science, vol. 265, pp. 808-811 (1994).

Brewster, J.L., et al., "An Osmosensing Signal Transduction Pathway in Yeast", Science, vol. 259, pp. 1760-1763 (1993).

Rouse, J., et al., "A Novel Kinase Cascade Triggered by Stress and Heat Shock that Stimulates MAPKAP Kinase-2 and Phosphorylation of the Small Heat Shock Proteins", Cell, vol. 78, pp. 1027-1037 (1994).

Lee, J.C., et al., "A Protein Kinase Involved in the Regulation of Inflammatory Cytokine Biosynthesis", Nature, vol. 372, pp. 739-746 (1994).

Sen, J., et al., "Intrathymic Signals in Thymocytes are Mediated by p38 Mitogen-Activated Protein Kinase", The Journal of Immunology, pp. 4535-4538 (1996).

Batchvarova, N., et al., "Inhibition of Adipogenesis by the Stress-Induced Protein CHOP (Gadd153)", The EMBO Journal, vol. 14, No. 19, pp. 4654-4661 (1995).

Freshney, N.W., et al., "A Novel Protein Kinase Cascade that Results in the Phosphorylation of Hsp27", Cell, vol. 78, pp. 1039-1049 (1994).

Zervos, A.S., et al., "Mxi2, a Mitogen-Activated Protein Kinase that Recognizes and Phosphorylates Max Protein", Proc. Natl. Acad. Sci. USA, vol. 92, pp. 10531-10534 (1995).

Geng, Y., et al., "Protein Tyrosine Kinase Activation is Required for Lipopolysaccharide Induction of Cytokines in Human Blood Monocytes", The Journal of Immunology, vol. 151, No. 12, pp. 6692-6700 (1993).

Stein et al., Science vol. 261, pp. 1004-1012, Aug. 20, 1993.

McLaughlin, M.M., et al., "Identification of Mitogen-Activated Protein (MAP) Kinase-Activated Protein Kinase-3, a Novel Substrate of CSBP p38 MAP Kinase", The Journal of Biological Chemistry, vol. 271, No. 14, pp. 8488-8492 (1996).

Beyaert, R., et al., "The p38/RK Mitogen-Activated Protein Kinase Pathway Regulates Interleukin-6 Synthesis in Response to Tumour Necrosis Factor", The EMBO Journal, vol. 15, No. 8, pp. 1914-1923 (1996).

Shapiro, L., et al., "Specific Inhibition of P38 Mitogen Activated Protein (MAP) Kinase Inhibits in vitro HIV Replication in U1 Cells Induced by Interleukin (IL)-1, Tumor Necrosis Factor (TNF) or Phorbol Esters (PMA)", Eur. Cytokine Network, vol. 7, No. 3, Article No. 375 (1996).

Kumar, S., et al., "Activation of the HIV LTR by UV, Cytokines and High Osmolarity Requires CSBP/p38 Activation", Eur. Cytokine Network, vol. 7, No. 3, Article No. 380 (1996).

Han, J., et al., "Molecular Cloning of Human p38 MAP Kinase", Biochemica et Biophysica Act, vol. 1265, pp. 224-227 (1995).

Schmidtmayerova, H., et al., "Human Immunodeficiency Virus Type 1 Infection Alters Chemokine β Peptide Expression in Human Monocytes: Implications for Recruitment of Leukocytes into Brain and Lymph Nodes", Proc. Natl. Acad. Sci. USA, vol. 93, pp. 700-704 (1996).

Ho, D.D., et al., "Rapid Turnover of Plasma Virions and CD4 Lymphocytes in HIV-1 Infection", Nature, vol. 373, pp. 123-126 (1995).

* cited by examiner

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 18
      (B) TYPE: nucleic acid
      (C) STRANDEDNESS: single

```
        (D) TOPOLOGY: unknown (ii) MOLECULE TYPE: MAPKK sense (xi) SEQUENCE DESCRIPTION: SEQ ID NO: 1:

GCAGGAGCTG AACAAGAC                                                   18

(2) INFORMATION FOR SEQ ID NO: 2:

(i) SEQUENCE CHARACTERISTICS:
        (A) LENGTH: 17
        (B) TYPE: nucleic acid
        (C) STRANDEDNESS: single
        (D) TOPOLOGY: unknown (ii) MOLECULE TYPE: MAPKK antisense (xi) SEQUENCE DESCRIPTION: SEQ ID NO: 2:

TCTTGTTCAG CTCCTGC                                                    17
```

GUANYLHYDRAZONES USEFUL FOR TREATING DISEASES ASSOCIATED WITH T CELL ACTIVATION

CROSS REFERENCE TO RELATED APPLICATION

This application is a continuation of U.S. patent application Ser. No. 09/705,581, filed Nov. 2, 2000, now U.S. Pat. No. 6,673,777, which is a divisional of U.S. patent application Ser. No. 08/970,973, filed Nov. 14, 1997, now U.S. Pat. No. 6,143,728, which claims benefit of U.S. Provisional Application Ser. No. 60/031,061, filed Nov. 15, 1996. The entirety of these applications are incorporated herein by reference.

TECHNICAL FIELD OF THE INVENTION

The present invention provides a genus of guanylhydrazone-substituted compounds that are useful for treating various diseases associated with T cell activation and retroviral infection. The present invention is based upon the mechanistic discovery that the p38 mitogen activated protein kinase (MAPK) signaling pathway is inhibited by guanylhydrazone-substituted compounds.

BACKGROUND OF THE INVENTION

The human immunodeficiency virus (HIV) has been implicated as the primary cause of the slowly degenerative immune system disease termed acquired immune deficiency syndrome (AIDS) (Barre-Sinoussi et al., *Science* 220:868-870, 1983; Gallo et al., *Science* 224:500-503, 1984). In humans, HIV replication occurs prominently in $CD4^+T$ lymphocyte populations, and HIV-infection leads to depletion of this cell type and eventually to immune incompetence, opportunistic infections, neurological dysfunctions, neoplastic growth, and ultimately death. HIV is a member of the lentivirus family of retroviruses (Teich et al., *RNA Tumor Viruses,* 1984, Weiss et al., eds., CSH-Press, pp. 949-956). Other retroviruses include, for example, oncogenic viruses such as human T cell leukemia viruses (HTLV-I,-II,-III), and feline leukemia virus.

HIV-infection is pandemic and HIV-associated diseases represent a major world health problem. Although considerable effort is being put into the design of effective therapeutics, currently no curative anti-retroviral drugs against AIDS exist. For example, virally encoded reverse transcriptase has been one focus of drug development. A number of reverse-transcriptase-targeted drugs, including 2',3'-dideoxynucleoside analogs such as AZT, ddI, ddC, 3TC, and d4T have been developed which have been shown to been active against HIV (Mitsuya et al., *Science* 249:1533-1544, 1990). While beneficial, these nucleoside analogs are not curative (Larder et al., *Science* 243:1731-1734, 1989). In addition, the drugs often cause toxic side effects such as bone marrow suppression, vomiting, and liver function abnormalities.

The late stages of HIV replication, which involve crucial virus-specific processing of certain viral encoded proteins, have also been suggested as possible anti-HIV drug targets. Late stage processing is dependent on the activity of a viral protease, and drugs are marketed which inhibit this protease (Erickson, *Science* 249:527-533, 1990). Thus, although a great deal of effort is being directed to the design and testing of anti-retroviral drugs, effective, non-toxic treatments are still needed.

Mitogen Activated Protein (MAP) kinases are important mediators of signal transduction from the cell surface to the nucleus. The ERK1 and ERK2 mammalian subtype of the MAP kinase family have been cloned. Two additional subtypes have been discovered, p38 MAP kinase and c-jun kinase (JNK) which may be activated independently and simultaneously. The ERK pathway is activated by growth factors or phorbol esters (Marshall, *Cell* 80:179-185, 1995). In contrast, p38 MAP kinase and JNK pathways are activated by inflammatory cytokines and cellular stresses such as heat shock, osmotic stress or ultraviolet light (Galcheva-Gargova et al., *Science* 265:806-808, 1994; Kyriakis et al., *Nature* 369:156-160, 1994; and Raingeaud et al., *J. Biol. Chem.* 270:7420-7426, 1995).

Mammalian p38 MAP kinase was identified in murine pre-B cells transfected with the LPS-complex receptor, CD14, and in murine macrophages where it is activated in response to LPS (Han et al., *Science* 265:808-811, 1994). p38 has been identified as the mammalian homologue of yeast osmosensing MAP kinase, HOG1 (Brewster et al., *Science* 259:1760-1763, 1993), and the Xenopus kinase Mpk2 (Rouse et al., *Cell* 78:1027-1037, 1994). CSBP1 and CSBP2 have been identified as human homologues of murine p38 MAP kinase (Lee et al., *Nature* 372:739-746, 1994). p38 MAPK activation has also been identified in lymphocytes during intra-thymic signaling essential for the differentiation and repertoire selection of mature T-cell development (Sen et al., *J. Immunol.* 156:4535, 1996). Once activated by phosphorylation, p38 MAPK acts both transcriptionally and translationally to phosphorylate downstream targets. Such targets include the transcription factors ATF-2, CHOP, HSP27, Max (Raingeaud et al., *J. Biol. Chem.* 270:7420, 1995; Batchvarova et al., *EMBO J.* 14:4654, 1995; Freshney et al., *Cell* 78:1039, 1994; and Zervos et al., *Proc. Natl. Acad. Sci. USA* 92:10531, 1995), and the protein kinases MAPK activated protein kinase-2 and -3 (MAPKAP-K2 and-K3) (McLaughlin et al., *J. Biol. Chem.* 271: 8488, 1996; and Beyaert et al., *EMBO J.* 15:1914, 1996).

p38 MAP kinase is activated in TNF-treated cells and plays a selective role in gene induction, controlling, for instance, synthesis of IL-6 and granulocyte macrophage colony stimulating factor (GM-CSF) (Beyart et al., *EMBO J.* 15:1914-1923, 1996). The role of p38 in the signaling pathway for cytokine responses was further shown in studies using model systems of cytokine induction of HIV gene expression constructs to measure the effects of inhibiting p38. Using a laboratory cell line chronically infected with latent HIV, certain pharmaceutical inhibitors of p38 MAPK were reported to block the cytokine-induced production of HIV p24 (Shapiro et al., *Eur. Cytokine Netw.* 7:557, 1996). p38 inhibitors were also reported to block the cytokine-specific induction of HIV LTR-driven expression of an unrelated reporter molecule in a transfection model system (Kumar et al., *Eur. Cytokine Netw.* 7:558, 1996).

In view of the multitude of roles played in intracellular signaling by p38 MAP kinase, there is a need in the art to find compounds that will inhibit intracellular signaling pathways through p38 MAP kinase. Such selective inhibitors of this signaling pathway will inhibit T cell activation and therefore show therapeutic utility for treating infections caused by retroviruses (for example, HIV) and for various autoimmune diseases (for example, rheumatoid arthritis, lupus, graft versus host, host versus graft, insulin-dependent diabetes, and multiple sclerosis).

SUMMARY OF THE INVENTION

The present invention provides therapeutic modalities for the treatment of diseases and disorders caused as a result of T cell activation, in particular HIV-infection, by virtue of the p38 MAPK cellular signaling pathway as a target of intervention. The present invention specifically provides guanylhydrazone-substituted compounds to treat disorders and diseases related to T cell activation and HIV-infection. The present invention also relates to the use of other compounds which inhibit the p38 MAP kinase pathway in treating immune diseases, and other diseases or clinical conditions in which T lymphocytes and cytokines and/or other mediators released by activated T lymphocytes are implicated in the pathology of the disease condition.

The present invention also relates to therapeutic modalities for the treatment of disorders and diseases related to T cell activation, in particular HIV-infection, by administering an effective amount of a p38 MAPK pathway inhibitor in combination with at least one other therapeutic agent. Preferably the p38 MAPK pathway inhibitor is used in combination therapy with an antiviral agent of another class (i.e., treatment mechanism of action), such as a reverse transcriptase inhibitor (e.g., AZT, ddI, ddC, 3TC); an HIV protease inhibitor (e.g., ABT-538); or a preintegration complex inhibitor.

The invention is based on the discovery that the p38 MAPK signal transduction pathway participates in T lymphocyte co-stimulation. p38 MAPK activity was found to be enhanced in human T lymphocytes stimulated with a-CD3 and a CD28. Inhibition of the p38 MAPK pathway, by the addition of an exemplary multivalent guanylhydrazone, CNI-1493, resulted in inhibition of activation of the T lymphocytes, as measured by 1L-2 synthesis.

The various modalities of treatment described herein were designed on the basis of the proposed model. In particular, multivalent guanylhydrazone compounds, small organic molecules, antisense molecules, ribozymes and triple helix molecules targeted to the p38 MAP kinase pathway may be used to inhibit T cell activation and HIV-infection. In a specific embodiment of the invention, multivalent guanylhydrazone compounds, such as CNI-1493, may be used to inhibit HIV-infection. In yet another embodiment of the invention, upstream and downstream components of the p38 MAP kinase pathway may be targeted to inhibit HIV-infection. For example, MAPKAP kinase-2, which is downstream of p38 MAP kinase, may be targeted by antisense, ribozyme or triple helix molecules, to inhibit HIV-infection.

The present invention further relates to screening assays to identify compounds which inhibit the p38 MAP kinase pathway and may be used to treat diseases or disorders related to T cell activation, in particular HIV-infection.

BRIEF DESCRIPTION OF THE DRAWINGS

In FIGS. 2B, 2C and 2D PHA-activated T cells were pretreated with control diluent or various concentrations of CNI-1493 for one hour, infected with HIV 1-LAV as in FIG. 1, and cultured for 10 days.

DETAILED DESCRIPTION OF THE INVENTION

Definitions

"p38 MAP kinase" refers to the related homolog or analog belonging to the mammalian family of p38 kinase activity, including, for instance, the human members of the family, CSBP1 and CSBP2.

"p38 MAPK signaling pathway" or "p38 MAPK pathway" refers to both the upstream and downstream components of the signaling cascade.

Guanylhydrazone-Substituted Therapeutic Compounds

The present invention provides a method for treating retroviral-caused infection and autoimmune diseases, comprising administering an effective amount of a multivalent guanylhydrazone compound. The genera of guanylhydrazone compounds to be included in the present invention is described herein. The synthesis of guanylhydrazone compounds is also provided by the present invention and is also described in U.S. Pat. No. 5,599,984, incorporated herein by reference in its entirety. The terms "GhyCH—" shall mean NH$_2$(CNH)—NH—N=CH— and "GhyCCH$_3$—" shall mean NH$_2$(CNH)—NH—N=CCH$_3$—. The guanylhydrazone-substituted compounds shall include formula 1:

wherein $X_2$=GhyCH—, GhyCCH$_3$— or H—; $X_1$, $X'_1$, and $X'_2$ independently =GhyCH— or GhyCCH$_3$—; Z=-NH(CO)NH—, —($C_6H_4$)—, —($C_5NH_3$)— or -A-($CH_2$)$_n$-A-, n=2-10, which is unsubstituted, mono- or di-C-methyl substituted, or a mono or di-unsaturated derivative thereof; and A, independently, =—NH(CO)—, —(CO)NH—, —NH(CO)NH—, —NH— or —O— and salts thereof. For ease of synthesis, a preferred embodiment includes those compounds wherein A is a single functionality. Also included are compounds having the same formula 1 wherein $X_1$ and $X_2$=H; $X'_1$ and $X'_2$ independently=GhyCH— or GhyCCH$_3$—; Z=-A-($CH_2$)$_n$-A-, n=3-8; and A=-NH(CO)—, —(CO)NH— or —NH(CO)NH—, and salts thereof. Also included are compounds wherein $X_1$ and $X_2$=H; $X'_1$ and $X'_2$ independently=GhyCH— or GhyCCH$_3$— and Z=-O—($CH_2$)$_2$—O—.

Further examples of genera include: The genus wherein: $X_2$=GhyCH—, GhyCCH$_3$— or H—; $X_1$, $X'_1$, and $X'_2$=GhyCH— or GhyCCH$_3$—; and Z=-O—($CH_2$)$_n$—O—, n=2-10 and salts thereof; and the related genus wherein, when $X_2$ is other than H, $X_2$ is meta or para to $X_1$ and wherein $X'_2$ is meta or para to $X'_1$. A compound having the above formula wherein: $X_2$=GhyCH, GHyCCH$_3$ or H; $X_1$, $X'_1$, and $X'_2$, =GhyCH— or GhyCCH$_3$—; and Z=-NH—(C=O)—NH— and salts thereof; and the related genus wherein, when $X_2$ is other than H, $X_2$ is meta or para to $X_1$ and wherein $X'_2$ is meta or para to $X'_1$.

Also included are compounds having a formula 2:

wherein: n=3-8; $X_2$ and $X'_2$=GhyCH—, GhyCCH$_3$— or H—; $X_1$ and $X'_1$=GhyCH— or GhyCCH$_3$—; and salts thereof; and the related genus wherein, when $X_2$ or $X'_2$ or both are other than H, then $X_2$ or $X'_2$ are meta or para to $X_1$ or $X'_1$, respectively.

The compounds of the present invention can be synthesized by means of two fundamental reactions. Numerous variants may be synthesized by means of these reactions and that these variants have properties in common with the compounds herein.

Reaction 1 consists of the reaction of a substituted aromatic having a primary or secondary amine, e.g., 3,5-diacetylaniline, and a dioyl dichloride, e.g., glutaryl dichloride, to yield the corresponding N,N'-diphenylalkanediamide. "Reversed" diamides can also be prepared. Acetyl and diacetylbenzoic acid can be prepared by the reaction of the corresponding substituted toluenes and KMnO$_4$. The acids may be then activated by standard techniques and reacted with the appropriate α,ω-alkanediamines to yield the reverse "diamides". Mixed forward and reversed diamides can be synthesized by methods well known in the field of peptide synthesis. Thus, an N-t-butyloxycarbonyl amino acid may be reacted with a substituted aniline, followed by deprotection and reaction of the amino group with an activated substituted benzoic acid. When used herein the symbol "—NH(CO)—", unless otherwise indicated, includes the —(CO)NH— isomer.

The method is not limited to dioyl dichlorides. The trichloride derivatives of trioyl compounds may be used to synthesize triphenyl alkanetriamides in a similar fashion. Suitable triacids include cyclic acids, e.g., 1,3,5-cyclohexanetricarboxylic acid (Aldrich Chem. Co.), 1,3,5-trimethyl, 1,3,5-cyclohexanetricarboxylic acid (Kemp's triacid, Kemp and Petrakis, 1981, *J. Org. Chem.* 46:5140), 1,3,5-benzinetricarboxylic acid (Aldrich Chem. Co.) and linear tricarboxylic acids such as 1,2,3-propanetricarboxylic acid (Sigma Chem. Co.). The identical reaction may be performed wherein the dioyl chloride is replaced by trichloromethyl chloroformate to yield a diphenylurea condensation product. An alternative to Reaction 1 can be performed to yield a 1,n-(n-alkanedioxy) diarylene by reacting the 1,n-dibromoalkane, e.g., 1,2 dibromoethane and a monohydroxylarylene, e.g., 3-hydroxyacetophenone.

Further embodiments of the invention include the use of triamines of the form $H_2N$—$(CH_2)_n$—$NH$—$(CH_2)_q$—$NH_2$ wherein (n,q=2-6) and of the form Y—(($CH_2)_n$—$NH_2$)$_3$ wherein Y may be one of N (n=2-6), C(NO$_2$) (n=3), a C-alkane (n=1), 1,3,5-adamantanetriyl (n=3) or 1,3,5-benzinetriyl (n=1-3).

In two further embodiments, an acetyl- or diacetylaryl isocyanate is reacted with an alkanediamine or, alternatively, an acetyl- or diacetylaryl amine is reacted with an alkanediyl diisocyanate to yield bis-ureido intermediates which may be reacted with aminoguanidine to form the guanylhydrazone end products. The requisite isocyanates are either commercially available or may be synthesized from the corresponding amines by reaction with phosgene, trichloromethyl chloroformate, or bis(trichloromethyl) carbonate in toluene or xylene at elevated temperature.

Reaction 2 consists of the reaction of an acetophenone or benzaldehyde type moiety and an aminoguanidine to yield the condensation product wherein an imino-bonded (N=C) aminoguanidine replaces the ketone or carbonyl moiety of the arylene thus forming a guanylhydrazone and accompanied by the release of a water molecule.

P38 MAP Kinase Pathway

The present invention relates to therapeutic modalities and pharmaceutical compositions which target the p38 MAP kinase pathway for the treatment of diseases and disorders related to T cell activation, in particular HIV-infection. The present invention relates to a variety of techniques and compositions which may be utilized to inhibit T cell activation and HIV-infection. Such techniques may include, but are not limited to, gene therapy approaches, drugs, small organic molecules identified to inhibit the p38 MAP Kinase pathway.

Without being limited by any theory regarding the mode of action of the multivalent guanylhydrazones, these compounds may work by disrupting the p38 MAPK pathway. p38 MAP kinase pathway plays a critical role in the activation of human T lymphocytes and this pathway is inhibited by the multivalent guanylhydrazone compounds. Moreover, treatment of T cell cultures with multivalent guanylhydrazone compounds inhibited HIV-infection, as did inhibition of the p38 MAPK pathway by antisense molecules directed to the p38 MAPK sequence. The p38 MAP kinase pathway is activated when T lymphocytes are stimulated with either an antibody to CD3 or an antibody to CD28, and significantly activated when T lymphocytes were co-stimulated with both antibodies. The activation of the p38 MAP kinase pathway was inhibited by the addition of a multivalent guanylhydrazone to the stimulated T lymphocytes. In addition, the stimulation of the T lymphocytes was also inhibited by the addition of the multivalent guanylhydrazone, as measured by IL-2 secretion.

The necessity of p38 MAP kinase activation in HIV-infection of T cells was determined from experiments in which p38 MAPK activity was blocked by the addition of specific inhibitors of p38 MAPK expression, p38 MAPK antisense oligonucleotides. The necessity of p38 MAPK pathway activation to support HIV-infection was further demonstrated by the ability of p38 MAPK pathway inhibitor, CNI-1493, a multivalent guanylhydrazone, to inhibit HIV-infection in primary T cells. These results show that the p38 MAP kinase pathway plays a critical role in T cell activation and in the ability of T cells to support HIV-infection.

Among the compounds useful to disrupt the activity of p38 MAP kinase and the other components of its signaling pathway are antisense, ribozyme and triple helix molecules. Such molecules are designed to inhibit expression of the target genes, p38 MAP kinase or the other components of its signaling pathway.

Anti-sense RNA and DNA molecules act to directly block the translation of mRNA by hybridizing to targeted mRNA and preventing protein translation. With respect to antisense DNA, oligodeoxyribonucleotides derived from the translation initiation site, that is, between the −10 and +10 regions of the target gene nucleotide sequence of interest, are preferred.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Treatment of Autoimmune Diseases Characterized by T Cell Activation

The present invention relates to the use of compounds which inhibit T cell activation and/or which inhibit the p38 MAP kinase pathway as a method of treating disorders related to T cell activation. In particular the invention relates to the use of multivalent guanylhydrazone compounds and antisense molecules as a method of treating disorders related to T cell activation. The compounds of the present invention have utility in treating disorders which result from an inappropriate, rather than an insufficient immune response. Examples of such disorders, include but are not limited to, atopic conditions (IgE-mediated allergic conditions), such as asthma, allergy, including allergic rhinitis, dermatitis, including psoriasis, pathogen susceptibilities, chronic inflammatory disease, organ-specific autoimmunity including multiple sclerosis, Hashimoto's thyroiditis and Grave's disease, graft rejection, and graft-versus-host disease. Other immune disorders involving T cell activation include, but are not limited to, chronic inflammatory diseases and disorders, such as Crohn's disease, systemic lupus erythematosus, myasthenia gravis, thyroiditis, reactive arthritis, including Lyme disease, insulin-dependent diabetes, contact dermatitis, gastrointestinal allergies, including food allergies, eosinophilia, conjunctivitis, glomerular nephritis, certain pathogen susceptibilities such as helminthic (leishmaniasis), gram positive superantigen-induced shock, and certain viral infections, including HIV, and bacterial infections, including tuberculosis and lepromatous leprosy.

As described above, because of their pharmaceutical properties, the compounds of the present invention can be used especially as agents to treat patients suffering from disorders related to T cell activation. Such compounds can be administered to a patient either alone, or in pharmaceutical compositions where it is mixed with suitable carriers or excipient(s).

Screening Assay

The following assays are designed to identify compounds that interfere with or inhibit the p38 MAP kinase signaling pathway and, as a result, inhibit the activation of T cells. Compounds may include, but are not limited to, guanylhydrazone-substituted compounds according to formula 1 or formula 2 herein, and anti-p38 MAPK antisense oligonucleotides. Those compounds identified as inhibitors of the p38 MAP kinase pathway would have utility in treatment of disease or disorders related to T cell activation.

The assay identifies compounds which inhibit p38 MAP kinase pathway and, as a result, T cell activation. The assays of the present invention may include in vitro kinase assays which measure the effects of test compounds on the individual components of the p38 MAP kinase signaling pathway. For example, but not by limitation, these assays may involve measuring the effects of a test compound on a reaction mixture containing the test compound and a cell lysate prepared from activated T cells and a sufficient amount of time for the components to interact. p38 MAP kinase or another component of the pathway, such as MAPKAP-K2, is immunoprecipitated from the cell lysate and its kinase activity measured using a known substrate of the kinase, i.e., transcription factors AFT-2, CHOP, HSP27 and Max. The activity of the p38 MAP kinase component will be determined as a measurement of the phosphorylated state of the substrate. In order to test a compound for inhibitory activity, the reaction mixture is prepared in the presence and absence of the test compound. Control reaction mixtures are incubated without the test compound or with a placebo. The lack of phosphorylation of the substrate indicates that the MAP kinase is inhibited from interacting with or phosphorylating its substrate.

In a particular embodiment, the target substrate can be prepared for immobilization using recombinant DNA techniques routinely used in the art. For example, the target gene coding region can be fused to a glutathione-S-transferase (GST) gene using a fusion vector, such as pGEX-5X-1, in such a manner that its conformation is maintained in the resulting fusion protein. In such an assay, the GST-target gene fusion protein can be anchored to glutathione-agarose beads. The activated T cell lysate can be added in the presence or absence of the test compound in a manner that allows the kinase reaction to occur in the presence of $^{32}$P-ATP. At the end of the reaction period, unbound material can be washed away, and the substrate assayed for its phosphorylated state. The interaction between the target gene protein and the p38 MAP kinase pathway component can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular extract can be mixed together in a kinase buffer in the presence of $^{32}$P-ATP, but in the absence of the solid glutathione-agarose beads. The test compound can be added either during or after the species are allowed to interact. This mixture can then be added to the glutathione-agarose beads and unbound material is washed away. Again the extent of inhibition of the kinase reaction between the substrate target gene product and the component of the p38 MAP kinase pathway can be detected by measuring the radioactivity associated with the beads.

In addition, the assays of the present invention may include other in vivo assays to measure the effects of the test compounds on T cell activation. For example, test compounds may be assayed for their ability to inhibit activation of T cells. In such assays, test compounds may be added to T cells co-stimulated with a-CD3 and a-CD28. The stimulation of the T cells should result in the synthesis and secretion of cytokines, such as IL-2. The inhibition of the secretion or synthesis of such cytokines indicates that the test compound inhibits the activation of T cells.

Anti-Retroviral Combination Therapy

According to the present invention, multivalent guanylhydrazone compounds and inhibitors of the p38 MAPK pathway may be used in combination therapy for the treatment of retroviral infections, in particular HIV-infection. The guanyhydrazone-substituted compounds are used in combination with another antiviral agent or multiple antiviral agents to improve the overall antiviral effect. Such additional antiviral agents which may be used with multivalent guanylhydrazone compounds and p38 MAPK pathway inhibitors include but are not limited to those which function on a different target molecule involved in viral replication, such as, reverse transcriptase inhibitors, viral protease inhibitors, preintegration complex inhibitors, and glycosylation inhibitors.

Inhibitors of p38 MAPK pathway or a pharmaceutically acceptable derivative thereof can also be used in combination with retrovirus inhibitors, such as reverse transcriptase inhibitors, HIV protease inhibitors and preintegration complex inhibitors. Reverse transcriptase inhibitors include 3'azido-3'-thymidine (AZT) and dideoxyinosine (ddI), 2',3'-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3TC (sold under the brand name of Epivir®); 2',3'-dideoxy-2'-fluoronucleosides; 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides; and 2',3'-dideoxy-2',3'-didehydro-fluorothymidine (Fd4T). Preferably, the 2',3'-dideoxy-2'-fluoronucleosides of the invention are those in which the fluorine linkage is in the beta configuration, including, but not limited to, 2',3'-dideoxy-2'-beta-fluoroadenosine (F-ddA), 2',3'-dideoxy-2'-beta-fluoroinosine (F-ddI), and 2',3'-dideoxy-2'-beta-fluorocytosine (F-ddC). Such combinations allow one to use a lower dose of the nucleoside derivative thus reducing the toxicity associated with that agent, without loss of antiviral activity because of the use of the p38 MAPK pathway inhibitor. Moreover, such a combination reduces or avoids viral resistance, as the host cell rather than the virus is the target of the p38 MAPK inhibitors of the present invention.

Preferred combinations of p38 MAP kinase pathway inhibitors and nucleoside derivatives within the scope of the present invention include an effective amount of a multivalent guanylhydrazone-substituted compound and an effective amount of AZT to treat HIV-infection; and an effective amount of a multivalent guanylhydrazone compound and an effective amount of ddI, or an effective amount of a preintegration complex inhibitor, such as those described in U.S. Pat. No. 5,574,040, the disclosure of which is incorporated by reference herein.

Inhibitors of the p38 MAP kinase pathway can also be used in combination with uridine phosphorylase inhibitors, including acyclouridine compounds, including benzylacyclouridine (BAU); benzyloxybenzylacyclouridine (BBAU); aminomethyl-benzylacyclouridine (AMBAU); aminomethyl-benzyloxybenzylacyclouridine (AMB-BAU); hydroxymethyl-benzylacyclouridine (HMBAU); and hydroxymethyl-benzyloxybenzylacyclouridine (HMB-BAU).

According to the present invention, inhibitors of p38 MAPK pathway or a pharmaceutically acceptable derivative thereof can also be used in combination with cytokines or cytokine inhibitors, including but not limited to rIFN α, rIFN β, rIFN γ, IL-2, inhibitors of TNFα, and MNX-160. Human rIFN-αA (>108 IU/mg) and rIFN γ (1.4×108 IU/mg) can be obtained from Hoffman LaRoche. Human rIFN β Ser 17 (1.0×108 IU/mg) are obtained from Berlex Biosciences. IL-2 (interleukin-2) can be obtained commercially from Chiron. Reference standards are obtained from the World Health Organization (human IFNα WHO standard B,69,19 and human IFN β, WHO no. G-023-902-527, or the National Institute of Allergy and Infectious Disease, National Institute of Health no. G-023-901-530.

Inhibitors of p38 MAPK pathway can be used in combination with viral protease inhibitors, including but not limited to, MK-639 (Merck), Invirase (saquinavir, Roche), ABT-538 (Abbott, CAS Reg. No. 155213-67-5), AG1343, VX0478 (Burroughs Wellcome/Glaxo, CAS Reg. No. 161814-49-9), DMP450, SC-52151 (Telinavir). Protease inhibitors are generally thought to work primarily during or after assembly (i.e., viral budding) to inhibit maturation of virons to a mature infectious state. For example, ABT-538 has been shown to have potent antiviral activity in vitro and favorable pharmokinetic and safety profiles in vivo (Ho et al., *Nature* 373:123-126, 1995). Administration of ABT-538 to AIDS patients causes plasma HIV-1 levels to decrease exponentially and CD4 lymphocyte counts to rise substantially. The exponential decline in plasma viraemia following ABT-538 treatment reflects both the clearance of free virions and the loss of HIV-1 producing cells as the drug substantially blocks new rounds of infection. ABT-538 treatment reduces virus-mediated destruction of CD4 lymphocytes. Combining this treatment with inhibitors of the p38 MAP kinase pathway, which inhibits at a different stage of HIV-infection, would be likely to have synergistic effects and have a dramatic clinical impact.

Inhibitors of p38 MAPK pathway or a pharmaceutically acceptable derivative thereof can also be used in combination with a class of anti-HIV drugs which interfere with 5'-mRNA processing, for example ribavirin. (Ribavirin (Virazole) from Viratel Inc.). Although the mechanism of action of ribavirin is not clear, this drug is thought to compete with guanosine in the formation of mRNA cap structures and/or interfere with the functional methylation of these molecules. In addition, inhibitors of p38 MAPK pathway can be used in combination with therapeutic agents, such as Amphotericin B (Fungizone, obtained from Gibco) a polyene microlide antifungal antibiotic which interacts with sterols and binds to them irreversibly. Amphotericin B represents a unique class of agents that are active against a variety of lipid-enveloped viruses, including HIV. Although amphotericin B exhibits severe in vivo toxicities, the methyl ester form of this drug also exhibits anti-HIV activity and has a low cellular toxicity profile in vitro. Therefore amphotericin B or its methyl ester can be used in combination therapy with inhibitors of p38 MAPK pathway.

Inhibitors of the p38 MAPK pathway can also be used in combination with inhibitors of glycoprotein processing, such as castonospermine (Boehringer Mannheim). Castanospermine is a plant alkaloid which inhibits glycoprotein processing, and acts as an anti-HIV since HIV contains two heavily glycosylated proteins, gp120 and gp41. Protein glycosylation plays an important role in gp120 interaction with CD4. Under conditions of infection by progeny virions synthesized in the presence of castanospermine, the infectivity of HIV was attenuated.

Preferred combinations to be used within the methods of treating HIV include the use of an effective amount of a multivalent guanylhydrazone-substituted compound and an effective amount of ddI; the use of an effective amount of a multivalent guanylhydrazone compound and an effective amount of 3TC; and the use of an effective amount of a multivalent guanylhydrazone-substituted compound and an effective amount ribavirin.

Therapeutic Uses, Routes of Administration and Formulations

The inhibitors of p38 MAPK pathway may be used for antivirals effects against viral infection other than HIV, such as HBV, EBV, CMV, and other opportunistic infections including TB. Effective doses of the combination therapy as described below may be formulated in suitable pharmacological carriers and may be administered by any appropriate means, including, but not limited to injection (intravenous, intraperitoneal, intramuscular, subcutaneous), by absorption through epithelial or mucocutaneous linings (oral mucosa, rectal and vaginal epithelial linings, nasopharyngeal mucosa, intestinal mucosa); orally, transdermally or any other means available within the pharmaceutical arts.

A compound can be administered to a human patient by itself or in pharmaceutical compositions where it is mixed with suitable carriers or excipients at doses to treat or ameliorate various conditions involving T cell activation and viral infection. A therapeutically effective dose further refers to that amount of the compound sufficient to inhibit T cell activation and/or HIV-infection. Therapeutically effective doses may be administered alone or as adjunctive therapy in combination with other treatments for HIV-infection or associated diseases. Techniques for the formulation and administration of the compounds of the instant application may be found in "Remington's Pharmaceutical Sciences" Mack Publishing Co., Easton, Pa., latest addition.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome coated with an anti-CD4 antibody. The liposomes will be targeted to and taken up selectively by cells expressing CD4.

The pharmaceutical compositions may be manufactured by means of conventional mixing, dissolving, dragee-making, levitating, emulsifying, encapsulating, entrapping, or lyophilizing processes. Pharmaceutical compositions for use in accordance with the invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated by combining the active compounds with pharmaceutically acceptable carriers. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For administration by inhalation, the compounds for use according to the invention are delivered in the form of an aerosol spray presentation from pressurized packs or a nebulizer, with the use of a suitable propellant, such as, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, such as, by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulary agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle before injection, such as, sterile pyrogen-free water.

Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the p38 MAPK signaling pathway may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate salts, and the like.

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Dosage amount and interval may be adjusted individually to provide plasma levels of the active moiety which are sufficient to maintain the desired modulating effects, or minimal effective concentration (MEC). The MEC will vary for each compound but can be estimated from in vitro data; such as, the concentration necessary to achieve a 50-90% inhibition of HIV-infection using the assays described herein. Dosages necessary to achieve the MEC will depend on individual characteristics and route of administration. However, HPLC assays, bioassays or immunoassays can be used to determine plasma concentrations.

The amount of composition administered will be dependent on the subject being treated, on the subject's weight, the severity of the affliction, the manner of administration and the judgment of the prescribing physician.

EXAMPLE 1

This example illustrates an experiment showing that an exemplary guanylhydrazone-substituted compound, CNI-1493 (N,N'-bis(3,5-diacetylphenyl)decanediamide tetrakis(amidinohydrazone) tetrahydrochloride) inhibited the p38 MAP kinase pathway. CNI-1493 has been shown to inhibit TNF production by macrophages activated by LPS. CNI-1493 blocked the synthesis of a 26 kDA membrane form of TNF, indicating that protein translation was inhibited. Further evidence for the mechanism of translation suppression was given by experiments using constructs in which the 5'UTR and the 3'UTR of TNF to drive expression of a reporter molecule. Both the 5'UTR and the 3'UTR regions of the TNF gene were required to elicit maximal translation suppression by CNI-1493. The effect of CNI-1493 on p38 MAPK was next determined as p38 MAPK has been implicated in the regulation of TNF translation. The pretreatment of human PBMC's with CNI-1493, resulted in the suppression of p38 MAPK activity after the addition of LPS. These results indicates that CNI-1493 specifically inhibits activation of the p38 MAPK signal transduction pathway in LPS-mediated TNF production.

EXAMPLE 2

This example illustrates an experiment showing that the p38 MAP kinase pathway participates in T lymphocyte co-stimulation. Co-stimulation of T lymphocytes occurs when two independent signals are applied to T cells, such as immobilized α-CD3 and soluble α-CD28, resulting in T cell activation and, among other manifestations, production of IL-2. Two members of the MAPK family of signal transduction molecules, ERK and JNK, have previously been implicated in T cell co-stimulation. p38 MAPK has been shown to play a role in during the activation of monocytes and macrophages, however little is known about the role p38 MAPK function in T cells.

For studies of human T cells, buffy coats were obtained by elutriation from normal human donors to the Long Island Blood Bank Services. Peripheral blood mononuclear cells (PBMC's) were isolated by density gradient centrifugation through Ficoll-Hypaque (Hypaque. Pharmacia); typically one preparation yielded $200 \times 10^6$ cells. T cells were isolated by passing through a T cell column (R&D) as per manufacturer's instructions. Jurkat cells were obtained from ATCC and maintained in DMEM containing 10% heat-inactivated fetal bovine serum, antibiotics and L-glutamine.

A rabbit polyclonal antibody against p38, and the recombinant GST-AFT2 plasmid where a gift of Dr. Roger Davis (Howard Hughes Institute, Worcester, Mass.). A GST-AFT2 fusion protein was purified by affinity chromatography using glutatione-agarose, as per manufacturer's instructions (Pharmacia, Inc.). The human monoclonal anti-CD3 antibody was purchased from Pharmingen and a human monoclonal anti-CD28 antibody was purchased.

Whole cell lysates were prepared using kinase lysis buffer, containing a final concentration of 20 mM Tris pH 7.5, 10% glycerol, 1% Triton X-100, 0.137M NaCl, 25 mM B-glycerophosphate, 2 mM EDTA, 1 mM orthovanadate, 2 mM pyrophosphate, 10 µg/ml Leupeptin, 1 mM PMSF. Proteins were fractionated on a 12% SDS-PAGE gel, transferred by electrophoresis to PVDF membranes (Biorad, Inc.) and probed with a 1:1000 dilution of a rabbit polyclonal antibody that immunospecifically recognizes phosphorylated human p38 MAPK (Santa Cruz Biotechnology, Inc.). Binding to antibody was detected using enhanced chemiluminescence (Amersham International PLC).

$2-5 \times 10^6$ cells were lysed after appropriate pretreatment in 500-1000 µl kinase lysis buffer and centrifuged at $14,000 \times g$ for 15 minutes at 4° C. Endogenous p38 was immunoprecipitated with polyclonal p38 antibody prebound to protein-A agarose for one hour at room temp. Agarose beads with immunoprecipitated p38 MAPK protein were washed twice with lysis buffer described above, and kinase assays performed by washing twice with kinase buffer (25 mM Hepes pH 7.4, 25 mM B-glycerophosphate, 25 mM $MgCl_2$, 2 mM dithiothreitol, 0.1 mM orthovanadate), and incubation with 5 µg of substrate protein (GST-ATF2), and 50 µM (gamma-$^{32}$P) ATP (10 Ci/mmol) in a final volume of 30 µl. The reactions were stopped after 30 minutes by boiling in an equivalent volume of 2X Laemmli sample buffer. The phosphorylated substrate was visualized using SDS-PAGE by autoradiography and phosphorlmager analysis (Amersham, Inc.).

T cell co-stimulation resulted in synergistic p38 kinase activity. To test whether p38 MAP kinase was stimulated during co-stimulation of T cells, antibodies to CD3 and CD28 were used singly and in combination against Jurkat cells in vitro. Jurkat cells were treated with either immobilized anti-CD3, soluble CD28 or both for one half hour, harvested and assayed for p38 MAP kinase activity by measuring the phosphorylation of a known p38 MAPK target, the transcription factor ATF2. Addition of CD3 alone stimulated p38 MAPK activity 3 fold, whereas addition of anti-CD28 alone stimulated p38 MAPK activity 5-fold. Co-stimulation by addition of both anti-CD3 and anti-CD28 antibodies resulted in synergistic p38 MAPK activity, increasing 12-fold. Co-stimulation by addition of both anti-CD3 and anti-CD antibodies resulted in synergistic p38 MAPK activity, increasing 12-fold over baseline levels, as measured densitometrically.

p38 MAPK activation was inhibited by CNI-1493 in monocytes and macrophages after stimulation with lipoplysaccharide, although it is not clear whether p38 MAPK or its upstream activators are the direct drug target. CNI-1493 was added to Jurkat cells exposed to anti-CD3, anti-CD28 or both anti-CD3+anti-CD28 to test whether this agent could inhibit the p38 MAPK activity induced by co-stimulation. The observed inhibition of p38 MAP kinase activity by CNI-1493 was dose-dependent. Although anti-CD3 stimulation was unaffected by CNI-1493, stimulation of p38 MAPK was inhibited approximately 50%, and co-stimulation with anti-CD3 and anti-28 was inhibited completely at a dose of 1.5 µM anti-CD28. Thus, CNI-1493 inhibited p38 MAP kinase activity stimulated during T cell co-activation.

EXAMPLE 3

This example illustrates a role for the p38 MAP kinase pathway in HIV-1 infection of primary T cells, specifically addressing the hypothesis that activation of p38 MAPK is required for HIV-1 infection of primary T lymphocytes. For studies of human T cells, buffy coats were obtained by elutriation from normal human donors to the Long Island Blood Bank Services. Peripheral blood mononuclear cells (PBMC's) were isolated by density gradient centrifugation through Ficoll-Hypaque (Hypaque, Pharmacia). Typically, one preparation yielded about $200 \times 10^6$ cells. T cells were isolated by passing through a T cell column (R&D) as per manufacturer's instructions. Jurkat cells were obtained from ATCC and maintained in DMEM containing 10% heat-inactivated fetal bovine serum, antibiotics and L-glutamine.

T cells were prepared by Ficoll-Hypaque separation, adherence exclusion of monocytes, and activation with PHA (5 µg/ml) for 3 days in RPMI 1640+10% FCS+L-glutamine+antibiotics (PS). After HIV 1-LAV stocks were prepared and titrated on CEM cells, T cells were washed and incubated with 1000 tissue culture infectious units (TCIU) of virus for 2 hours at 37 degrees C., washed and fresh medium added containing IL-2 20 U/ml. At various time points after infection, cell lysates were prepared.

A rabbit polyclonal antibody against p38, and a recombinant GST-AFT2 plasmid where a gift of Dr. Roger Davis (Howard Hughes Institute, Worcester, Mass.). A GST-AFT2 fusion protein was purified by affinity chromatography using glutatione-agarose as per manufacturer's instructions (Pharmacia, Inc.). Human monoclonal anti-CD3 antibody was purchased from Pharmingen and the human monoclonal anti-CD28 antibody was purchased.

Whole cell lysates were prepared using kinase lysis buffer containing a final concentration of 20 mM Tris pH 7.5, 10% glycerol, 1% Triton X-100, 0.137M NaCl, 25 mM B-glyceropliospliate. 2 mM EDTA. 1 mM orthovanadate. 2 mM pyrophospilate. 10 µg/ml Leupeptin. 1 mM PMSF. Proteins were fractionated on a 12% SDS-PAGE gel, transferred by electrophoresis to PVDF membranes (Biorad, Inc.) and probed with a 1:1000 dilution of a rabbit polyclonal antibody that immunospecifically recognizes phosphorylated human p38 MAPK (Santa Cruz Biotechnology, Inc.). Binding to antibody was detected using enhanced chemiluminescence (Amersham International PLC).

$2-5 \times 10^6$ cells were lysed after appropriate pretreatment in 500-1000 µl kinase lysis buffer and centrifuged at $14,000 \times g$ for 15 minutes at 4° C. Endogenous p38 was immunoprecipitated with polyclonal p38 antibody prebound to protein-A agarose for one hour at room temp. Agarose beads with immunoprecipitated p38 MAPK protein were washed twice with lysis buffer described above, and kinase assays performed by washing twice with kinase buffer (25 mM Hepes pH 7.4, 25 mM B-glycerophosphate, 25 mM $MgCl_2$ 2 mM dithiothreitol, 0.1 mM orthovanadate), and incubation with 5 µg of substrate protein (GST-ATF2), and 50 µM (gamma-$^{32}$P) ATP (10 Ci/mmol) in a final volume of 30 µl. The reactions were stopped after 30 minutes by boiling in an equivalent volume of 2× Laemmli sample buffer. The phosphorylated substrate was visualized using SDS-PAGE by autoradiography and phosphorimager analysis (Amersham, Inc.).

Figure 1A:
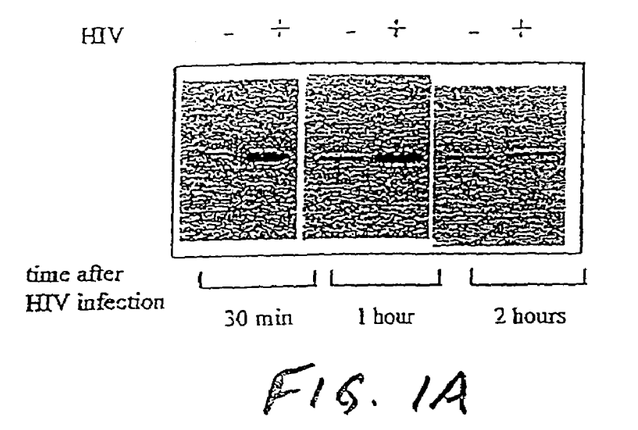
FIG. 1A depicts the protein immunoblot result of phospho-p38 MAPK levels in T cells in the absence (−) or presence (+) of HIV at various time points after infection.
Figure 1B:
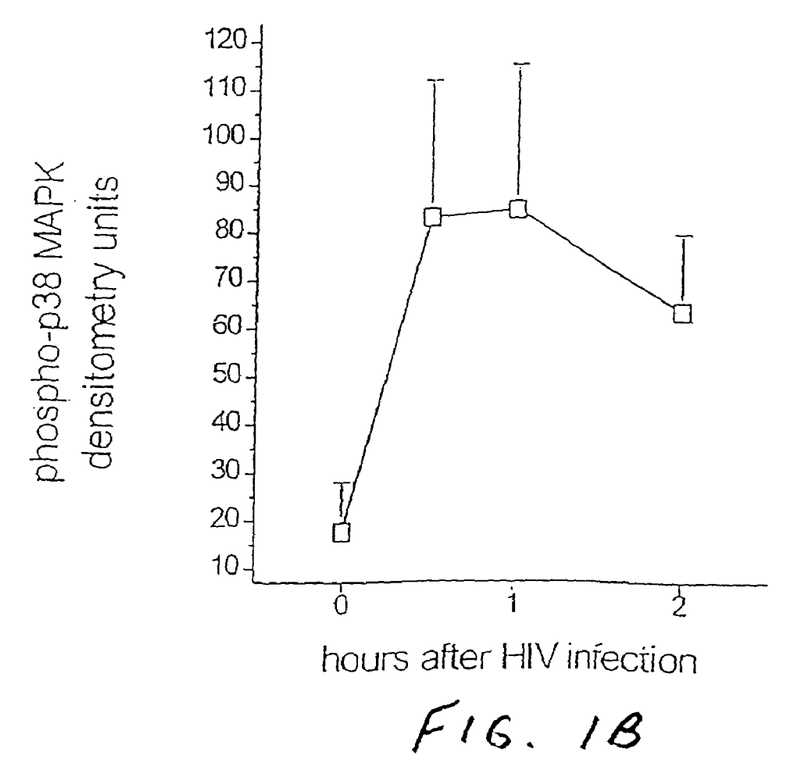
FIG. 1B shows the cumulative results of similar experiments on three donors (mean±standard error). These data show increased phosphorylation of p38 MAPK after primary infection of T cells.
Figure 2A:
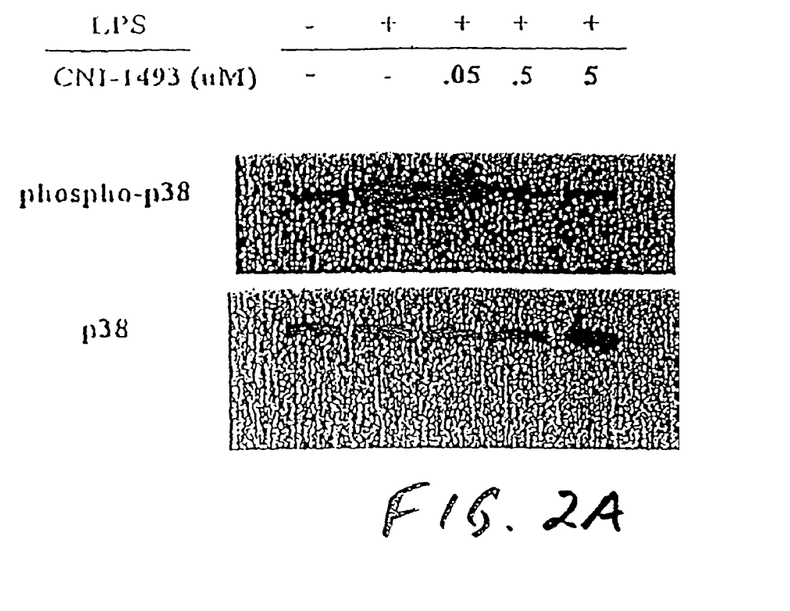
FIG. 2A shows that RAW 264.7 cells were pretreated with/without various concentrations of CNI-1493 one hour prior to addition of LPS (*Escherichia coli* 0111:B4 100 ng/ml; Sigma Chemical Co. St. Louis, Mo.). Cell lysates were prepared for immunoprecipitation and immunoblotting 15 minutes after administration of LPS.
Figure 2B:
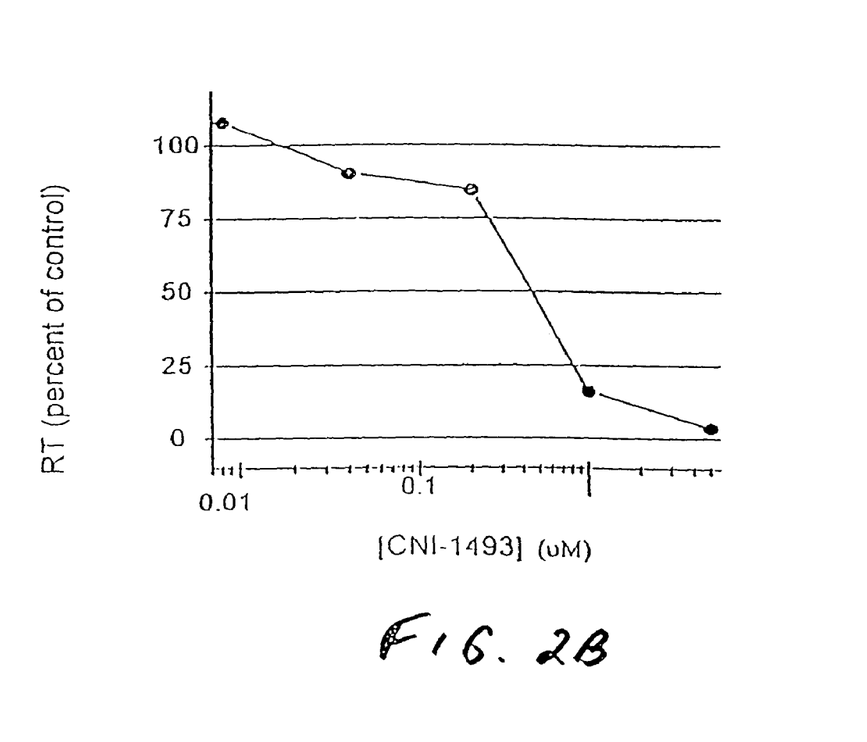
FIG. 2B is a graph of dose-dependent inhibition by CNI-1493 of HIV-infection as assessed by the accumulation of reverse transcriptase (RT) at day 6 of culture.
Figure 2C:
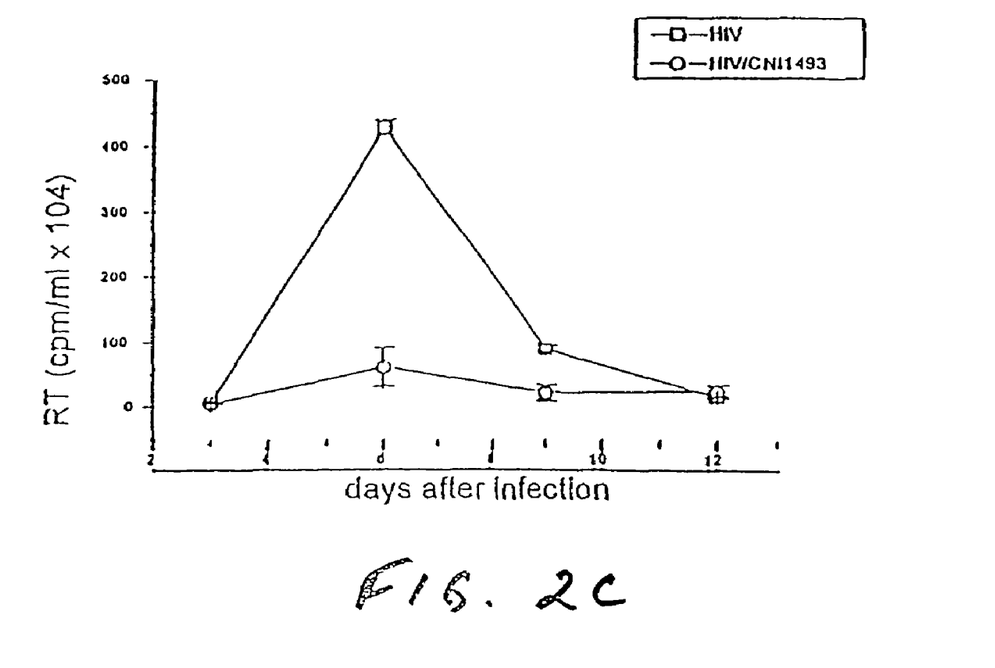
FIG. 2C is a graph of HIV inhibition by 1 mM CNI-1493 over time.
Figure 2D:
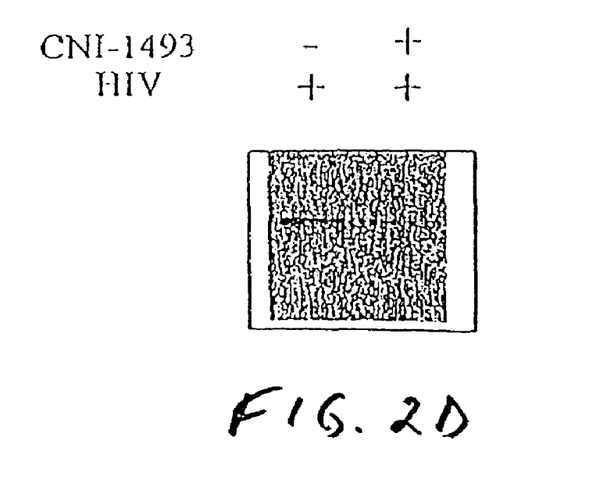
FIG. 2D is an immunoblot of phospho-p38 MAPK expression in HIV-1 infected cells on day 6 after culture treated with/without 1 mM CNI-1493. These data show inhibition of HIV replication by the exemplary guanylhydrazone substituted compound CNI-1493.
Figure 3:
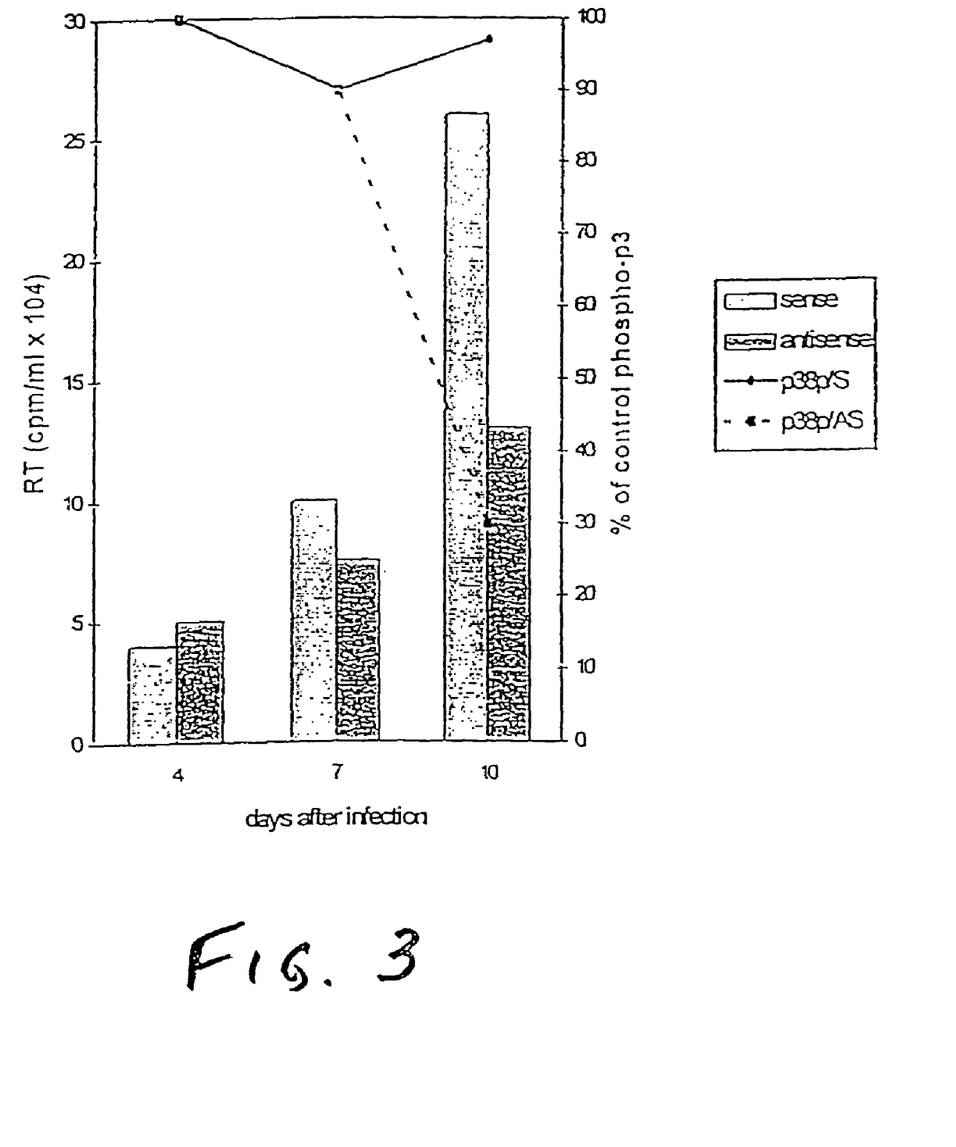
FIG. 3 shows that an 18-mer phosphothiorate oligonucleotides coding for bp 324-341 in either the sense (5'-GCAG-GAGCTGAACAAGAC-3' SEQ. ID. NO.:1) or antisense (5'-GTCTTGTTCAGCTCCTGC-3' SEQ. ID. NO.:2) direction were used based on the sequence for human p38 MAPK (Han et al., 1995 *Biochem. Biophys. Acta* 1265:224). T cells were infected with HIV 1-LAV in the presence of 1 mM 18-mer, refed every 3-4 days with media containing fresh oligomer and supernatants collected at various time points for RT assay. Simultaneously, cells were also plated, treated similarly and harvested for phospho-p38 MAPK levels assayed by immunoprecipitation at various time points as measured by RT assay. Shown in this figure is the effect of addition of sense and antisense p38 MAPK oligonucleotide on phospho-p38 levels and its correlation with HIV replication, as measured by RT. These data show that phosphothiorate antisense p38 MAPK oligonucleotides inhibit HIV replication in T cells.

For anti-sense experiments, 18-mer phosphothioate oligonucleotides coding for bp 324-341 in either the sense (5'GCAGGAGCTGAACAAGAC3' SEQ ID NO.:1) or anti-sense (5'GTCTTGTTCAGCTCCTGC3' SEQ ID NO.:2) directions were used, based upon the sequence for human p38 MAPK (Han et al., *Biochem Biophys. Acta* 1265:224, 1995). T cells were infected with HIV 1-LAV in the presence of 1 µM 18-mer, refed every 3-4 days with media containing fresh oligomer and supernatants collected at various time points for RT assay. Simultaneously, cells were also plated, treated similarly and harvested for phospho-p38 MAPK levels assayed by immunoprecipitation at varying time points. FIGS. 1-3 show the effect of addition of sense and antisense p38 MAPK oligonucleotide on phospho-p38 levels and its correlation with HIV replication, as measured by RT.

Primary T lymphocytes were isolated from normal donors stimulated with PHA for 2-3 days, and then infected with the LAV strain of HIV. As early as 30 minutes post-infection, a rapid increase in the phosphorylation of p38 MAP kinase was observed in HIV-infected cells, as compared to control uninfected cells (FIGS. 1A and 1B). Levels of p38 MAP kinase activity remained elevated (450% increase as compared to uninfected cells; $p < 0.05$ for up to 2 hours following introduction of virus into the cultured T cells. The magnitude of p38 activation in T cells as a consequence of HIV-infection correlated well with increases in p38 MAPK observed in macrophages following activation by known stimuli of p38 MAPK such as UV, TNF and LPS (Raingeaud et al., *J. Biol. Chem.* 270:27395, 1995). The kinetics of p38 MAPK activation in the two cell types were similar as well, remaining elevated for up to two hours but returning to basal levels within 6 hours.

These results suggest the possibility that HIV-1 infection of T cells requires activation of the p38 MAPK pathway. Primary T cells activated with PHA were pretreated (or not) with CNI-1493 for one hour, infected with the LAV strain of HIV, and RT activity measured at various time points after infection, up to 10 days. As shown in FIG. 2B, CNI-1493 inhibited HIV replication in T-cells in a dose-dependent manner, with an $IC_{50}$ of approximately 0.5 µM. A time course of the effect of CNI-1493 (1 µM) on HIV replication is shown in FIG. 2B. The effect of CNI-1493 on suppression of p38 MAP kinase activity during this period correlated with its suppressive effect on HIV replication (FIGS. 2C, 2D).

Further evidence for the necessity of p38 MAPK activation in T cell HIV-1 infection was obtained from experiments in which p38 MAP kinase activity was blocked by the addition of antisense oligonucleotides. Phosphothiorated sense and antisense p38 MAPK oligomers were added to LAV-infected primary T cells simultaneously with the virus, and then replenished every three days thereafter until day 10. The p38 MAP kinase antisense oligonucleotides decreased HIV replication proportionate to the decrease in phospho-p38 MAPK activity on both day 7 and day 10 after infection (FIG. 3). Thus, two independent methods that suppress p38 MAPK activation (CNI-1493 and antisense oligonucleotides) each inhibited HIV replication, suggesting that activating p38 MAPK is required for maximal HIV replication.

Figure 4A:
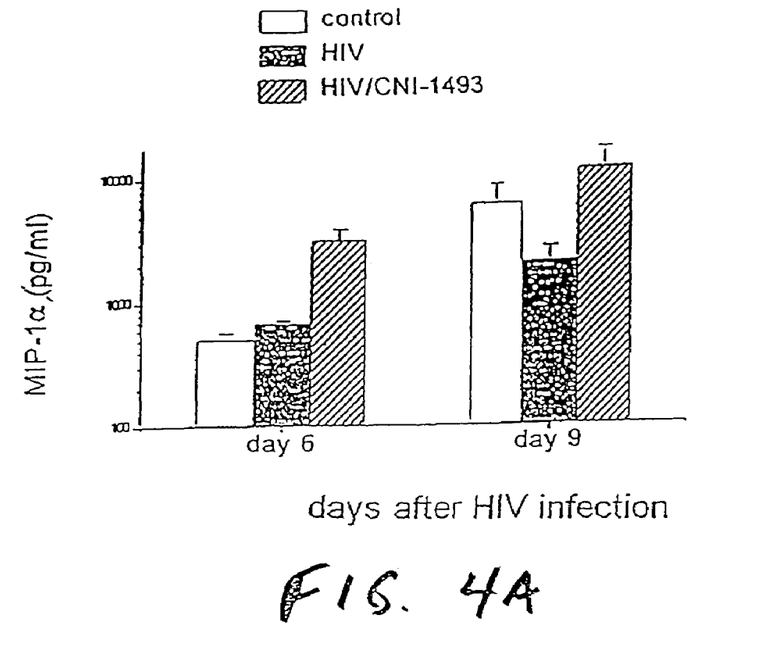
FIG. 4 shows the results of an experiment wherein T cells, prepared and infected with HIV 1-LAV (as described above), were grown and supernatants harvested and assayed for MIP-1α and MIP-1 levels by sandwich ELISA (Schmidtmayerova et al., 1996, *Proc. Natl. Acad. Sci. USA* 93:700)). Assays were done in triplicate and error bars represent standard deviation of the mean. The data shown here is the result of an individual donor experiment, showing that chemokine secretion of T cells is unchanged or slightly increased during CNI-1493-caused inhibition of HIV replication.
Figure 4B:
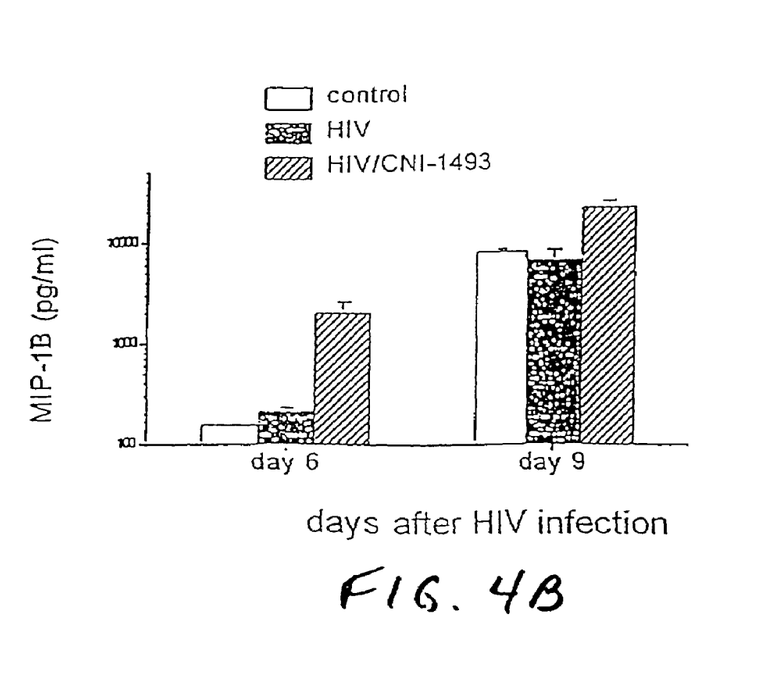

The CC-chemokines MIP-1α, MIP-1β and RANTES have recently been shown to inhibit HIV replication in T cells (Geng et al., *J. Immunol.* 151:6692, 1993) and it has been suggested these molecules may play a role in the host defense against viral infection. Because ideal anti-HIV therapies would not interfere with the ability of the host to mount its own defense, it was also evaluated whether inhibition of the p38 MAP kinase signal transduction pathway inhibits chemokine production in T cells. Levels of MIP 1α and MIP 1β during LAV infection of primary T cells were not decreased by CNI-1493 (FIG. 4). MIP 1α and 1β levels dropped slightly late in HIV-1 infection (day 9). In the presence of CNI-1493, however, chemokine levels either were slightly elevated (day 6) or normal (day 9). Thus, suppression of p38 MAP kinase activity during HIV-infection of T cells did not adversely affect one mechanism contributing to the cells' natural immunity against the virus, in the form of chemokine expression, while simultaneously inhibiting HIV replication.

When considered together, these results identify the p38 MAP kinase signal transduction pathway as critical for maximal in vitro infectivity of primary T-cells by HIV-1. Stimulation of p38 MAPK activity was early (within 30 minutes) after introduction of virus, and remained elevated up to 9 days post-infection. Inhibition of the p38 MAPK pathway by CNI-1493, as well as by p38 antisense oligonucleotides was able to reduce HIV replication, as measured by RT. The secretion of chemokines, potent natural immunoinhibitory molecules against HIV, is unaffected. Hence, p38 MAPK kinase represents a novel therapeutic target against primary HIV-infection of T cells.

We claim:

1. A method for treating HIV, comprising administering an effective HIV-treating amount of a guanylhydrazone-substituted compound to a subject known to have HIV, wherein the guanylhydrazone-substituted compound is CNI-1493.

2. The method according to claim 1, wherein said treating further comprises inhibiting a p38 MAP kinase signaling pathway and reducing HIV replication in said subject.

3. The method according to claim 1, further comprising administering an additional therapeutic agent.

4. The method according to claim 3, wherein the additional therapeutic agent is an anti-viral agent.

5. The method according to claim 3, wherein the additional therapeutic agent is a reverse transcriptase inhibitor.

6. The method according to claim 3, wherein the additional therapeutic agent is an HIV protease inhibitor.

7. The method according to claim 3, wherein the additional therapeutic agent is a preintegration complex inhibitor.

8. A method for treating HIV, comprising administering an effective HIV-treating amount of a guanylhydrazone-substituted compound to a subject known to have HIV, wherein the guanylhydrazone-substituted compound has the formula:

wherein $X_2$=GhyCH—, GhyCCH$_3$— or H—; $X_1$, $X'_1$ and $X'_2$, independently=GhyCH— or GhyCCH$_3$—; Z=—NH(CO)NH—, —(C$_6$H$_4$)—, —(C$_5$NH$_3$)— or -A-(CH$_2$)$_n$-A-, n=2-10, which is unsubstituted, mono- or di-C-methyl substituted, or a mono or di-unsaturated derivative thereof; and A independently=—NH(CO)—, —(CO)NH—, —NH(CO)NH—, —NH— or —O— and salts thereof.

9. The method of claim 8, further comprising administering one or more retrovirus inhibitor selected from the group consisting of reverse transcriptase inhibitor, HIV protease inhibitor, and preintegration complex inhibitor.

10. The method of claim 9, wherein the retrovirus inhibitor is one or more reverse transcriptase inhibitor selected from the group consisting of 3'azido-3'-thymidine (AZT); dideoxyinosine (ddI); 2',3'-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T); 3TC; 2',3'-dideoxy-2'-fluoronucleosides; 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; 2',3'-dideoxy-2',3'-didehydro-2'-fluoronucleoside; 2',3'-dideoxy-2',3'-didehydro-2'-fluorothymidine (Fd4T); 2'3'-dideoxy-2'-beta-fluoroadenosine (F-ddA); 2',3'-dideoxy-2'-beta-fluoroinosine (F-ddI); and 2',3'-dideoxy-2-beta-fluorocytosine (F-ddC).

11. The method of claim 8, wherein the guanylhydrazone-substituted compound is a salt.

12. The method of claim 11, wherein the salt is selected from the group consisting of hydrochloride, hydrobromide, hydroiodide, acetate, citrate, tartrate, lactate, and malate salt.

13. A method for treating HIV, comprising administering an effective HIV-treating amount of a guanylhydrazone-substituted compound to a subject known to have HIV, wherein the guanylhydrazone-substituted compound has the formula:

wherein $X_1$ and $X_2$=H; $X'_1$ and $X'_2$ independently=GhyCH— or GhyCCH$_3$—; Z=-A-(CH$_2$)$_n$-A-, n=3-8; and A=—NH(CO)—, —(CO)NH— or —NH(CO)NH—; and salts thereof.

14. A method for treating HIV, comprising administering an effective HIV-treating amount of a guanylhydrazone-substituted compound to a subject known to have HIV, wherein the guanylhydrazone-substituted compound has the formula:

wherein $X_1$, and $X_2$=H; $X'_1$ and $X'_2$ independently = GhyCH— or GhyCCH3—, and Z=—O—$(CH_2)_2$—O—, and salts thereof.

15. A method for treating HIV, comprising administering an effective HIV-treating amount of a guanylhydrazone-substituted compound to a subject known to have HIV, wherein the guanylhydrazone-substituted compound has the formula:

wherein $X_2$=GhyCH—, GhyCCH$_3$— or H—; $X_1$, $X'_1$ and $X'_2$=GhyCH— or GhyCCH$_3$—; and Z=—O—$(CH_2)_n$—O—, n=2-10, and salts thereof.

16. A method for treating HIV, comprising administering an effective HIV-treating amount of a guanylhydrazone-substituted compound to a subject known to have HIV, wherein the guanylhydrazone-substituted compound has the formula:

wherein n=3-8; $X_2$ and $X'_2$=GhyCH—, GhyCCH$_3$— or H—; $X_1$ and $X'_1$=GhyCH— or GhyCCH$_3$—; and salts thereof.

17. The method of claim 16, further comprising administering one or more retrovirus inhibitor selected from the group consisting of reverse transcriptase inhibitor, HIV protease inhibitor, and preintegration complex inhibitor.

18. The method of claim 17, wherein the retrovirus inhibitor is one or more reverse transcriptase inhibitor selected from the group consisting of 3'azido-3'-thymidine (AZT); dideoxyinosine (ddl); 2,3-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T); 3TC; 2',3'-dideoxy-2'-fluoronucleosides; 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; 2',3'-dideoxy-2',3'-didehydro-2'-fluoronucleoside; 2',3'-dideoxy-2',3'-didehydro-2'-fluorothymidine (Fd4T); 2'3'-dideoxy-2'-beta-fluoroadenosine (F-ddA); 2',3'-dideoxy-2'-beta-fluoroinosine (F-ddI); and 2',3'-dideoxy-2'-beta-fluorocytosine (F-ddC).

19. The method of claim 16, wherein the guanylhydrazone-substituted compound is a salt.

20. The method of claim 19, wherein the salt is selected from the group consisting of hydrochloride, hydrobromide, hydroiodide, acetate, citrate, tartrate, lactate, and malate salt.

* * * * *